(12) United States Patent
Livesay et al.

(10) Patent No.: US 9,159,209 B2
(45) Date of Patent: Oct. 13, 2015

(54) CONDUCTIVE FABRIC SEAL

(71) Applicant: UT-Battelle, LLC, Oak Ridge, TN (US)

(72) Inventors: Ronald Jason Livesay, Knoxville, TN (US); Brandon William Mason, New Market, MD (US); Michael Joseph Kuhn, Knoxville, TN (US); Nathan Carl Rowe, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 174 days.

(21) Appl. No.: 13/832,093

(22) Filed: Mar. 15, 2013

(65) Prior Publication Data

US 2014/0266265 A1    Sep. 18, 2014

(51) Int. Cl.
*G01R 27/08*    (2006.01)
*G08B 13/12*    (2006.01)

(52) U.S. Cl.
CPC .................. *G08B 13/126* (2013.01)

(58) Field of Classification Search
CPC ....... G01N 27/04; B65D 2101/00–2101/0092; G08B 13/126–13/128
USPC .......................................... 324/693, 706, 725
See application file for complete search history.

(56) References Cited

U.S. PATENT DOCUMENTS

| | | | | |
|---|---|---|---|---|
| 3,646,435 | A * | 2/1972 | Rozenson et al. | 324/725 |
| 4,558,308 | A * | 12/1985 | Ciordinik et al. | 340/550 |
| 4,598,274 | A * | 7/1986 | Holmes | 340/550 |
| 4,999,608 | A * | 3/1991 | Galomb | 340/550 |
| 5,677,674 | A * | 10/1997 | Wolf | 340/541 |
| 6,002,343 | A * | 12/1999 | Auerbach et al. | 340/10.41 |
| 6,031,457 | A * | 2/2000 | Bonkowski et al. | 340/572.1 |
| 6,690,183 | B2 | 2/2004 | Braun | |
| 7,274,289 | B2 | 9/2007 | Kerr et al. | |
| 7,360,439 | B2 | 4/2008 | Kuroda et al. | |
| 7,608,812 | B2 | 10/2009 | Beinhocker | |
| 7,646,299 | B2 | 1/2010 | Krill | |
| 7,978,070 | B2 | 7/2011 | Hunter | |
| 8,001,999 | B2 | 8/2011 | Schultz | |
| 2004/0210980 | A1* | 10/2004 | Cacioli et al. | 2/159 |
| 2008/0001741 | A1 | 1/2008 | Cobianu et al. | |
| 2008/0075934 | A1* | 3/2008 | Barlow et al. | 428/199 |
| 2012/0098663 | A1 | 4/2012 | Zhou et al. | |
| 2012/0196474 | A1 | 8/2012 | Selvitelli et al. | |

OTHER PUBLICATIONS

International Search Report and Written Opinion for PCT/US14/18176, 2014.

* cited by examiner

*Primary Examiner* — Patrick Assouad
*Assistant Examiner* — Demetrius Pretlow
(74) *Attorney, Agent, or Firm* — Colin L. Cini

(57) ABSTRACT

Disclosed are several examples of a system and method for detecting if an article is being tampered with. Included is a covering made of a substrate that is coated with a layer of an electrically conductive material that forms an electrically conductive surface having an electrical resistance. The covering is configured to at least partially encapsulate the article such that the article cannot be tampered with, without modifying the electrical resistance of the electrically conductive surface of the covering. A sensing device is affixed to the electrically conductive surface of the covering and the sensing device monitors the condition of the covering by producing a signal that is indicative of the electrical resistance of the electrically conductive surface of the covering. A measured electrical resistance that differs from a nominal electrical resistance is indicative of a covering that is being tampered with and an alert is communicated to an observer.

17 Claims, 19 Drawing Sheets

CONDUCTIVE FABRIC SEAL

STATEMENT REGARDING FEDERALLY SPONSORED RESEARCH AND DEVELOPMENT

This invention was made with government support under Contract No. DE-AC05-00OR22725 awarded by the U.S. Department of Energy. The government has certain rights in the invention.

CROSS-REFERENCE TO RELATED APPLICATIONS

None.

THE NAMES OF THE PARTIES TO A JOINT RESEARCH AGREEMENT

None.

BACKGROUND OF THE INVENTION

1. Field of the Invention

The present disclosure relates to security systems and methods and more specifically to systems and methods for providing an alert when an article or asset is tampered with.

2. Description of the Related Art

Each year, millions of articles are shipped in containers around the world via land, sea, and air transport modes. A container's time of arrival and time of departure at ports, customs, freight forwarders, and truckers, are typically tracked as the container progresses from its origin to its final destination. The tracking systems may include multiple, disparate systems, or a coordinated system as described in U.S. patent application Ser. No. 13/415,416, filed Mar. 8, 2012, and titled "Associative Tracking for Loosely-Coupled Supply Chain Networks", which is incorporated herein by reference in its entirety.

Tracking the progress of a container does not necessarily ensure that the article itself has not been damaged, corrupted, infiltrated, tampered with, or replaced, prior to arriving at its final destination. The ability to continuously monitor the physical condition of an article or shipping container is as important as tracking its location. This is especially important if the article being shipped contains special nuclear material, which could potentially be used by a terrorist group to construct an improvised explosive device or a dirty bomb.

Leakage of any material (liquid, gas or solid) from a shipping container is also a concern if the material is corrosive, caustic, radioactive or otherwise harmful to the surrounding environment or public. Monitoring the leakage of a material, especially a hazardous material, from a container can help prevent an uncontrolled spill and the associated environmental damage and cleanup expense.

U.S. Pat. No. 7,274,289, titled "System and Device for Detecting Object Tampering", describes a pattern of individual, insulated conductors that detects tampering by a change in continuity of a single conductor that is discovered by a sensor, which then communicates the event via a signal.

U.S. Pat. No. 7,646,299, titled "Anti-Tampering Security Material", describes a woven cloth having a fused conductor and accelerometer that detects tampering by a change in voltage and acceleration discovered by a sensor that communicates the event via a signal.

Electromagnetic interference or "EMI" comes from electronic devices and may be harmful to sensitive equipment and humans. A flexible substrate coated with a metallized coating, and manufactured by Swift Textile Metalizing, LLC of Bloomfield, Conn., U.S.A. protects sensitive equipment from the dangerous effects of EMI.

Despite the teachings provided by the prior art, further improvements to monitoring the physical condition of assets, items, articles, packages, and containers, and alerting personnel of a tampering condition are necessary.

BRIEF SUMMARY OF THE INVENTION

Disclosed are several examples of a system for detecting if an article is being tampered with. Included in the system is a covering made of a substrate that is coated with a layer of an electrically conductive material that forms an electrically conductive surface having an electrical resistance. The covering is configured to at least partially encapsulate the article such that the article cannot be tampered with, without modifying the electrical resistance of the electrically conductive surface of the covering. A sensing device is affixed to the electrically conductive surface of the covering and the sensing device monitors the condition of the covering by producing a signal that is indicative of the electrical resistance of the electrically conductive surface of the covering. A measured electrical resistance that differs from a nominal electrical resistance is indicative of a covering that is being tampered with and an alert is communicated to an observer.

Also disclosed are methods for monitoring the condition of an article. In a first step, a covering made of a substrate is coated with a layer of an electrically conductive material and forms an electrically conductive surface that has an electrical resistance is affixed around an article. The covering is configured to at least partially encapsulate the article such that the article cannot be tampered with, without modifying the electrical resistance of the covering. In a next step, an analog voltage value ($V_G$) is produced with a sensing device that is affixed to the electrically conductive surface of the covering. In the next step, the analog voltage value ($V_G$) is converted into a digital voltage value ($V_G$) with a data acquisition system. In the next step, a measured resistance $R_X$ is calculated from the digital voltage value ($V_G$) according to the equation $R_X=(R_2*R_3+R_3*(R_1+R_2)V_G/V_{in})/(R_1-(R_1+R_2)*V_G/V_{in})$ with a monitoring system. In the next step, the measured resistance ($R_X$) is compared to a known, nominal resistance ($R_{nominal}$) with the monitoring system. In a final step, an alert is generated with a signaling means if the measured resistance ($R_X$) is greater than the known, nominal resistance ($R_{nominal}$).

BRIEF DESCRIPTION OF THE SEVERAL VIEWS OF THE DRAWINGS

The present apparatus and method may be better understood with reference to the following drawings and description. Non-limiting and non-exhaustive descriptions are described with reference to the following drawings. The elements in the figures are not necessarily to scale, emphasis instead being placed upon illustrating principles. In the figures, like referenced numerals may refer to like parts throughout the different figures unless otherwise specified.

DETAILED DESCRIPTION OF THE INVENTION

Figure 1:
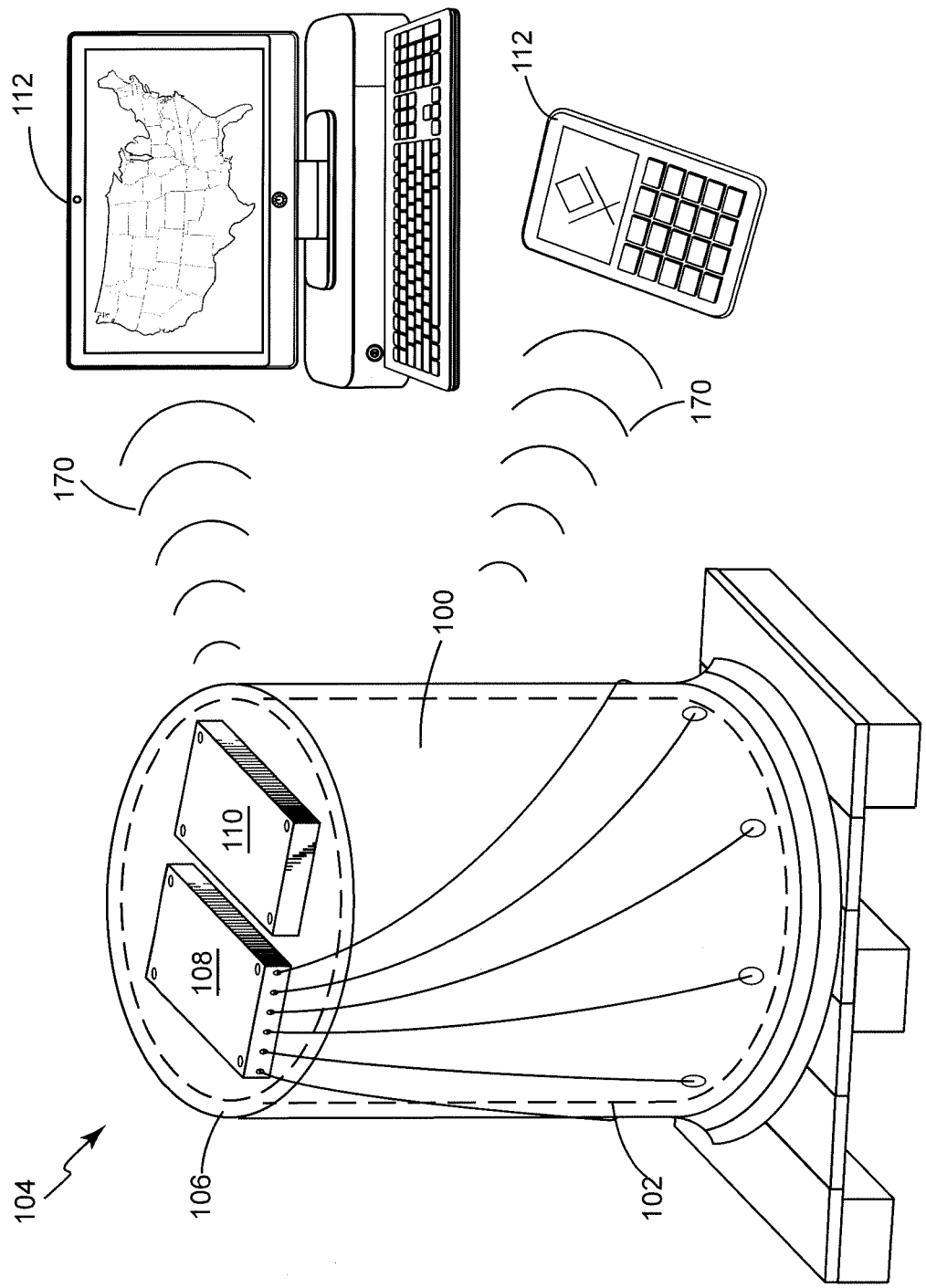
FIG. 1 is a schematic illustration of a conductive fabric seal device in accordance with an example of the present disclosure.

Referring first to FIG. 1, an important asset or an article 100 may be unpackaged, or packaged within a container 102 such as a box, a drum, or a crate, during shipping and storage. A tamper detection system 104 broadly includes a covering 106, a sensing device 108, a data acquisition system 110, and a monitoring system 112. Each element of the tamper detection system 104 will now be discussed in greater detail.

Figure 2:
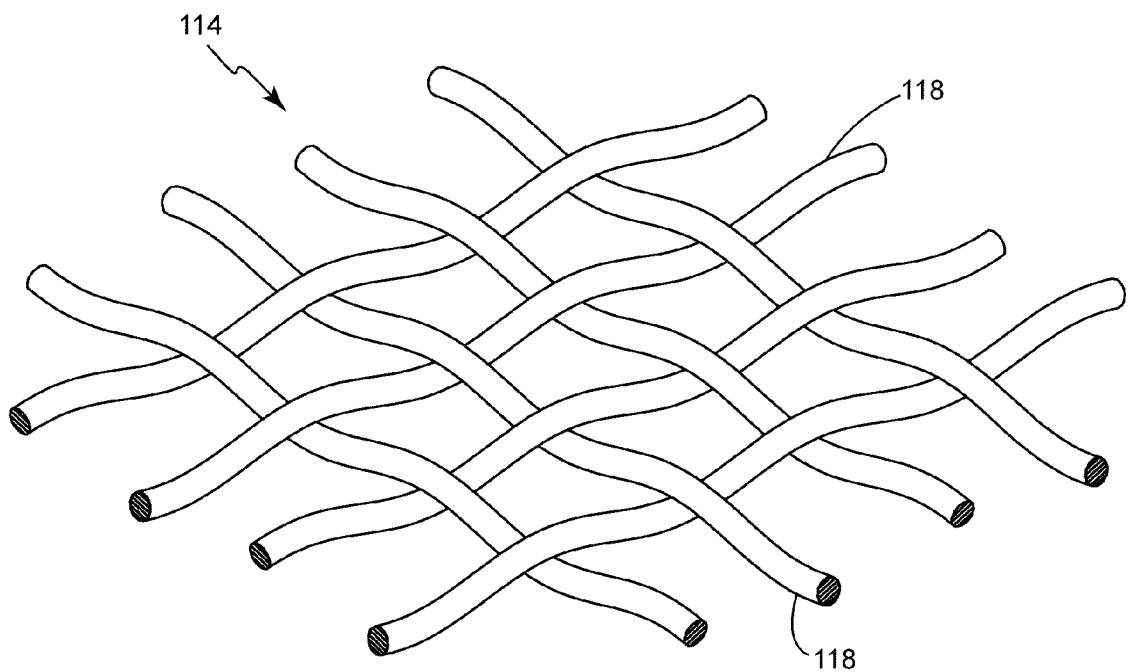
FIG. 2 is an illustration of an example of a fabric substrate portion of a covering.
Figure 3:
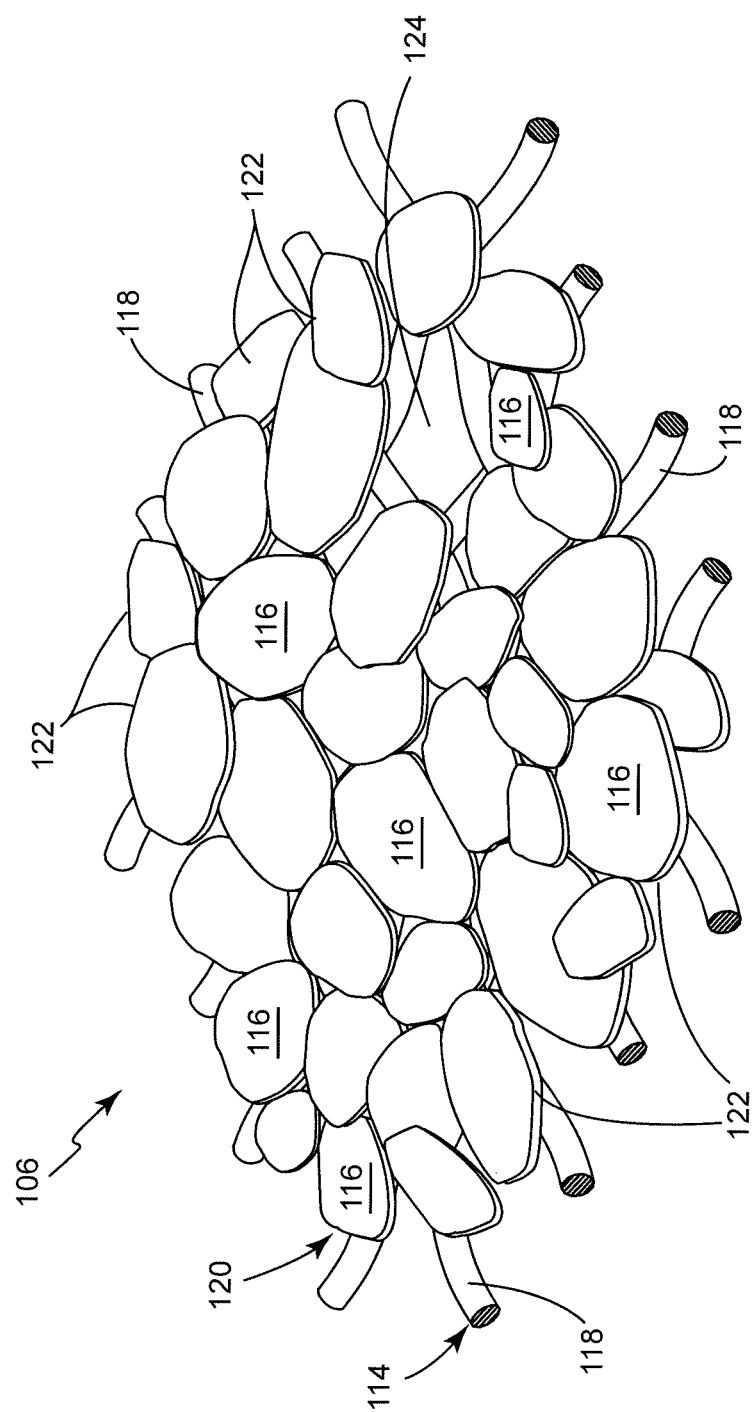
FIG. 3 is an illustration of an example of a coated fabric substrate portion of a covering.
Figure 4:
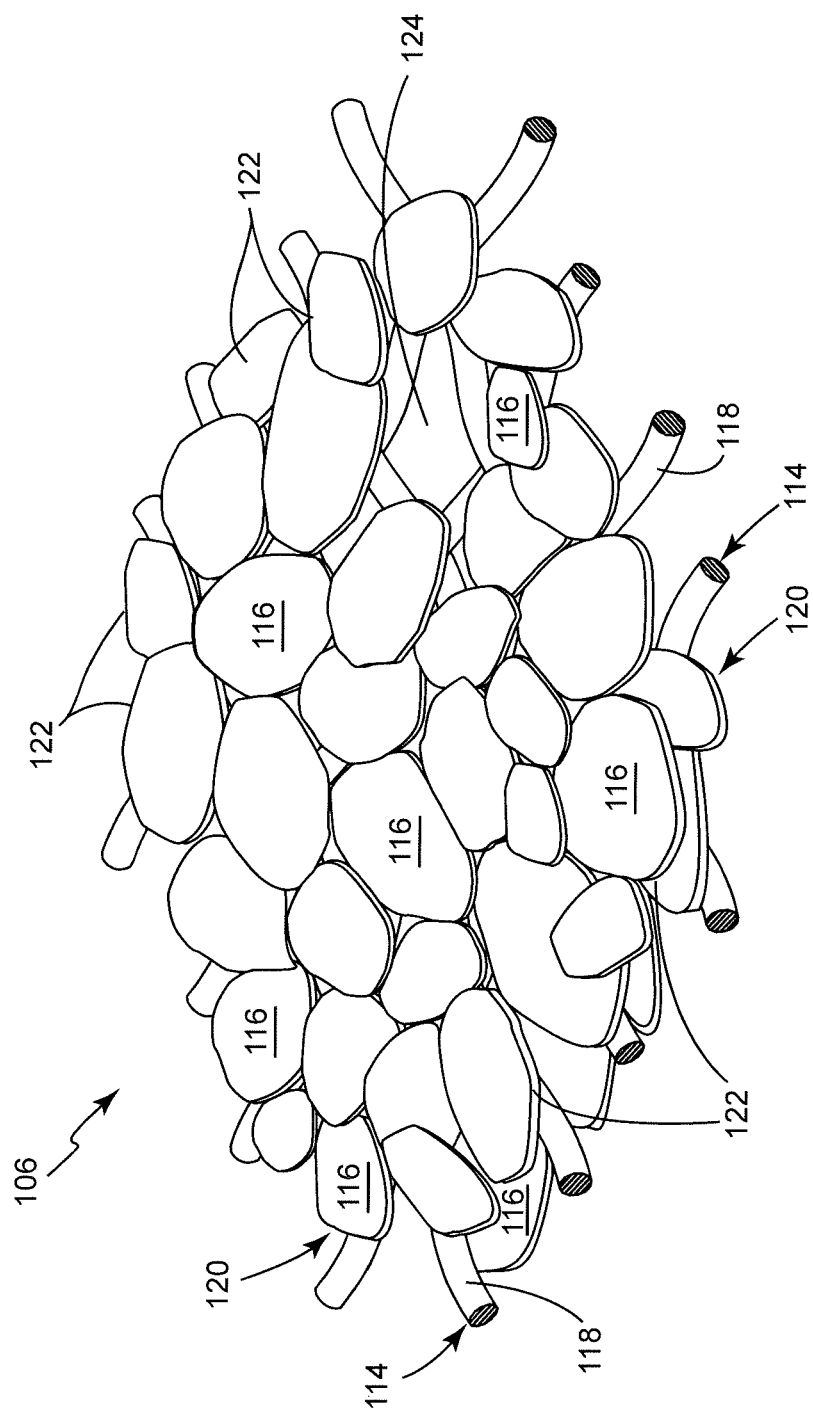
FIG. 4 is an illustration of another example of a coated fabric substrate portion of a covering.

With reference now to FIGS. 2-4, the covering 106 includes a substrate 114 that is coated with an electrically conductive material 116 in one or more layers. Once coated, the substrate 114 becomes metallized, thus forming a single, electrical conductor having an electrical resistance that can be measured and monitored for change.

The substrate 114 is comprised of individual fibers 118 that are made of an electrically insulative material. The fibers 118 are arranged in a woven (shown), unwoven, matt, or other arrangement. The fibers 118 must be strong, yet flexible, to allow the covering 106 to conform to the shape of the article 100 without experiencing any tearing or ripping damage during installation. For example, fibers 118 made of a synthetic material (e.g., nylon) or a natural material (e.g., silk, glass fiber) may be used to form the substrate 114.

Once the substrate 114 is formed, it is coated with one or more layers of the electrically conductive material 116. The layers of electrically conductive material 116 forms an electrically conductive surface 120 having an electrical resistance that can be measured and monitored for changes. A change in electrical resistance is indicative of a covering 106 that is being tampered with. Electrically conductive materials such as copper, nickel, silver, gold, brass, aluminum, or other conductive materials may be used as the electrically conductive material 116. The electrically conductive material 116 may be applied to a single side (FIG. 3) or both sides (FIG. 4) of the substrate 114.

The layer of electrically conductive material 116 may be applied to the substrate 114 using known coating methods such as chemical vapor deposition (CVD), electron beam physical vapor deposition (EBPVD), autocatalytic (electroless), electroplating, vacuum deposition, ion plating, sputtering, plasma spray, and electroless nickel plating for example. Other coating methods that can deposit electrically conductive material 116 to a nonconductive substrate 114 may also be used.

As shown in FIGS. 3-4, individual particles 122 form the layer of electrically conductive material 116 on the substrate 114. The particles 122 generally abut one another at their peripheries, but may also overlap one another as shown. In some areas, a gap 124 may be formed between adjacent particles 122 as shown. The gap 124 is insignificant, because an electrical conduction path is enabled through the particles 122 surrounding the gap 124. The particle 122 distribution density is controlled by the particle 122 size, the coating method used and the amount of time the substrate 114 is exposed during the coating process. Longer coating times will generally produce a denser, thicker, layer of electrically conductive material 116.

The covering 106 is configured to at least partially encapsulate an article 100 such that the article 100 cannot be tampered with, without changing the electrical resistance of the covering 106. In some examples, the covering 106 at least partially encapsulates the article 100 and in other examples, the covering 106 completely encapsulates the article 100. In effect, the covering 106 creates a shield, a veil, barrier, or a cloak around the article 100. In some examples, the covering 106 protects the article 100 from electromagnetic interference "EMI" when it is installed around the article 100.

Figure 5:
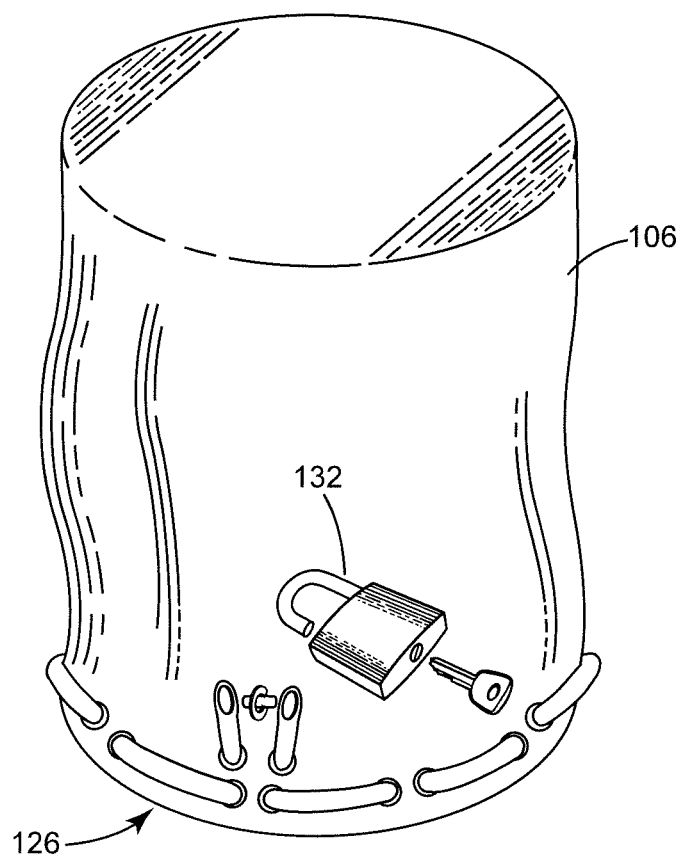
FIG. 5 is an illustration of an example of a covering affixed to an article with a fastening means.
Figure 6:
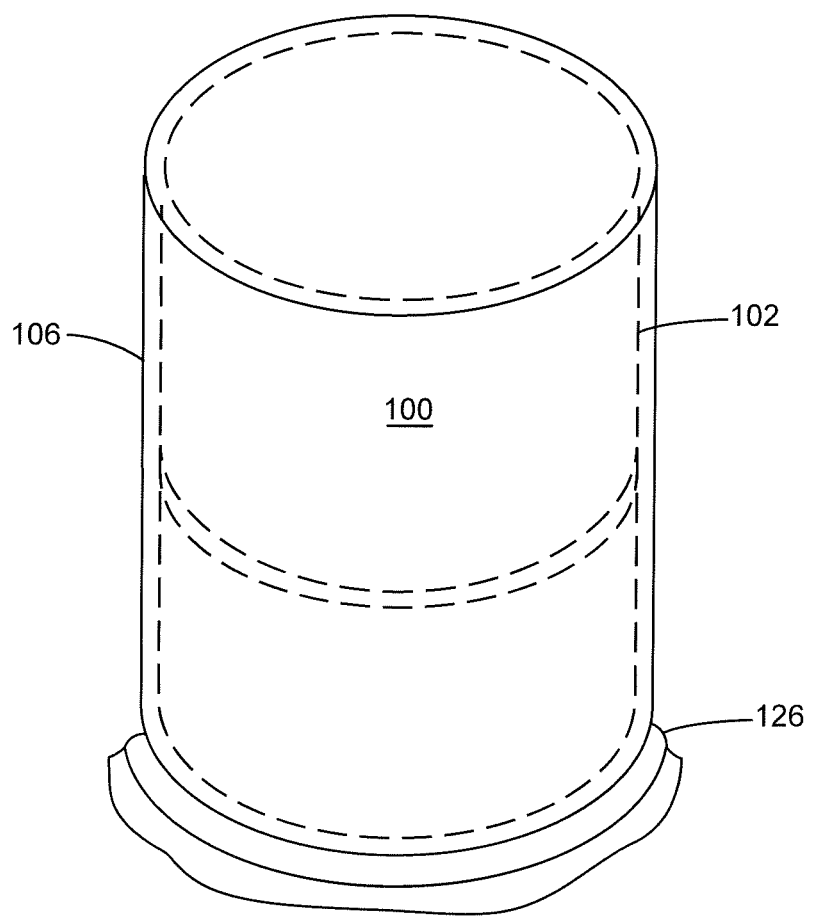
FIG. 6 is an illustration of an example of a covering affixed to a container with a fastening means.
Figure 7:
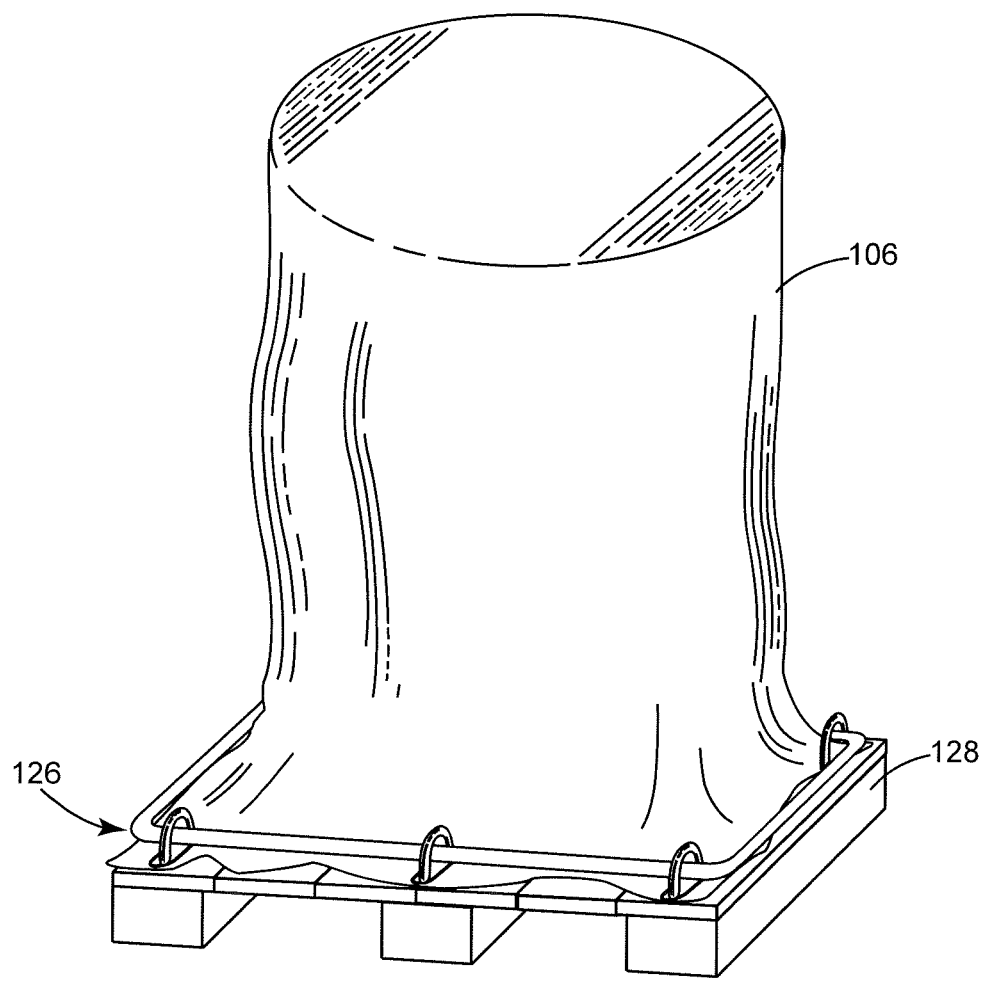
FIG. 7 is an illustration of an example of a covering affixed to a support with a fastening means.
Figure 8:
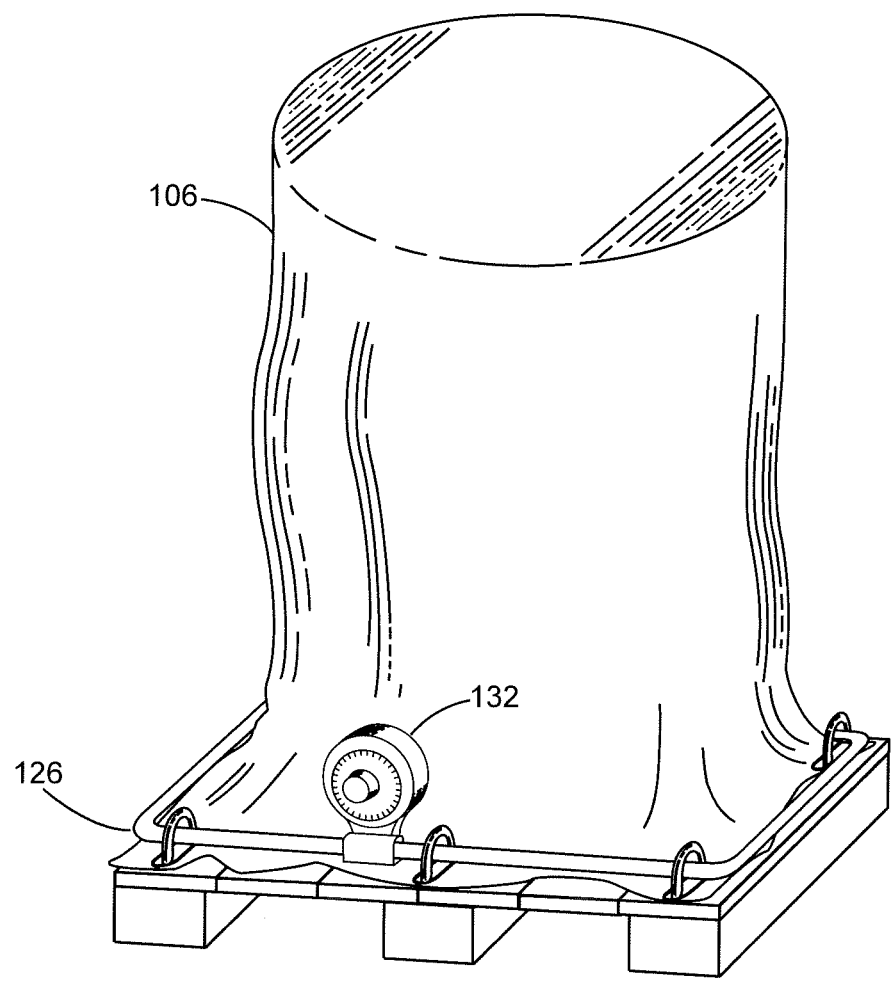
FIG. 8 is an illustration of an example of a covering affixed to a floor with a fastening means.

The covering may include fastening means 126 for securing the covering 106 to the article 100 so that the article 100 cannot be tampered with, without changing the electrical resistance of the covering 106. As illustrated in FIGS. 5-8, fastening means 126 such as a draw string, a metallized hook and loop fastener, electrically conductive glue, a mechanical fastener, a lock, heat shrink, or a compression fitting may be used. In the example of FIG. 5, the covering 106 is attached with the fastening means 126 to an article 100. In the example of FIG. 6, the covering 106 is attached with the fastening means 126, such as a compression fitting, to a container 102 housing an article 100. In the example of FIG. 7, the covering 106 is attached with the fastening means 126 to a platform 128 (e.g., pallet) that supports the article 100. In the example of FIG. 8, the covering 106 is attached with the fastening means 126 to a portion of flooring 130 that supports the article 100. The fastening means 126 may be a one-time use device, which must be destructively removed, or it may be a reusable device, which may be nondestructively removed by authorized personnel. Locking devices 132 that utilize physical keys or electronic keys would function in this application.

Figure 9:
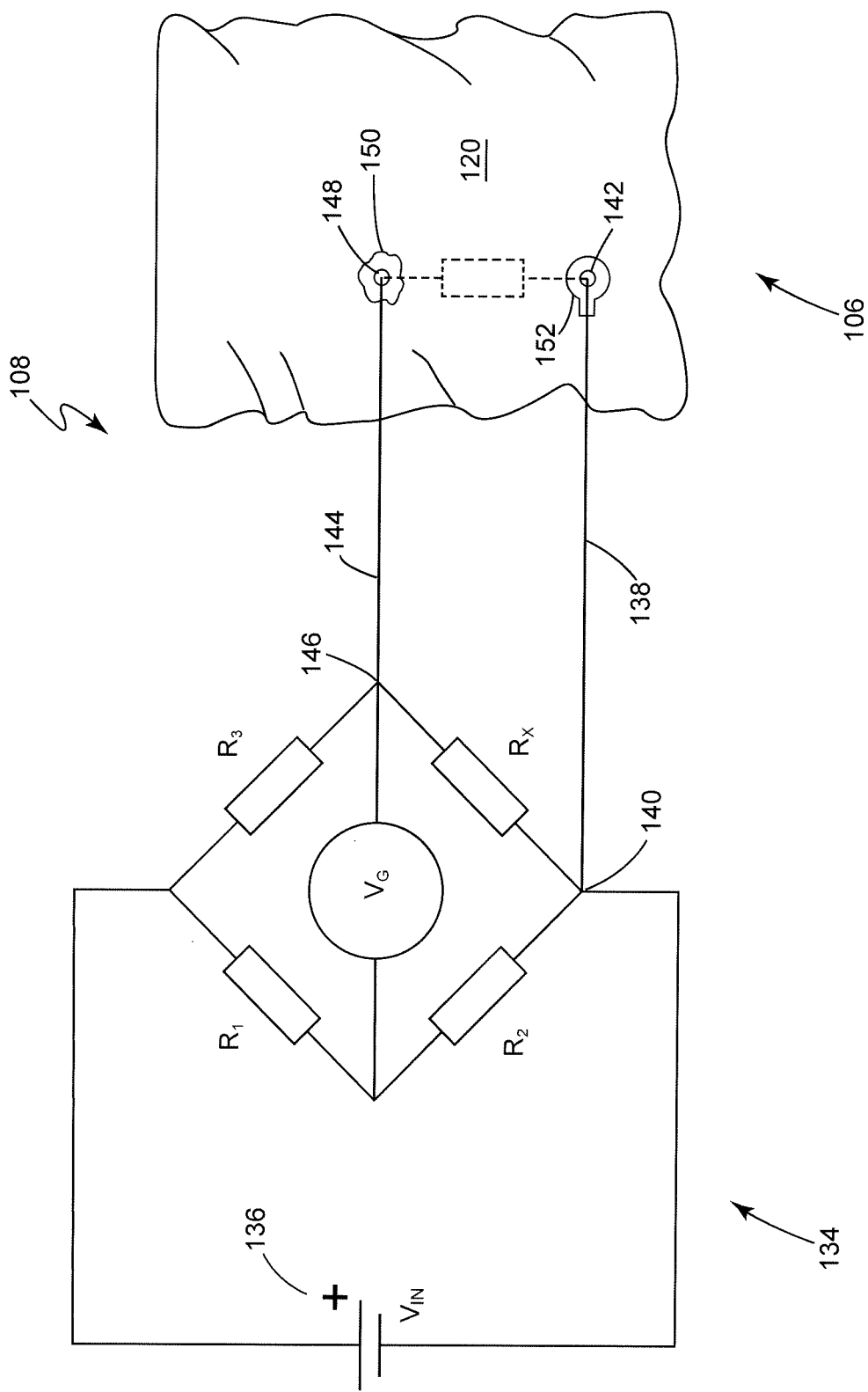
FIG. 9 is an illustration of a sensing device in accordance with an example of the present disclosure.

A sensing device 108, as illustrated in FIG. 9, determines the condition of the covering 106 by producing a signal that is indicative of the electrical resistance of the electrically conductive surface 120. The sensing device 108 includes a Wheatstone bridge circuit 134 having a power supply 136 (e.g. 9 Volts, 12 Volts, 120 Volts, 220 Volts, etc. . . . ), three known resistance legs $R_1$, $R_2$, $R_3$, and a measured resistance leg $R_X$. The voltage $V_G$ across the measured resistance leg $R_X$ of the circuit will vary in proportion to the resistance measured across the leg $R_X$. As the electrical resistance of the electrically conductive surface 120 increases, the measured voltage $V_G$ will decrease.

A measuring cable 138 electrically connects a first end 140 of the measured resistance leg $R_X$ to a measuring point 142 on the electrically conductive surface 120. A common cable 144 electrically connects a second end 146 of the measured resistance leg $R_X$ to a common point 148 on the electrically conductive surface 120. Note that the common point 148 is located at a different location on the electrically conductive surface than the measuring point 142. The area of the electrically conductive surface 120 disposed between the measuring point 142 and the common point 148 has an electrical resistance that is measurable and that is indicative of the condition of the electrically conductive surface 120 in that area. This area is illustrated in the figure as a phantom resistor. For example, a measured resistance $R_X$ that is indicative of a baseline electrically conductive surface 120 will be lower than a measured resistance $R_X$ of an electrically conductive surface 120 that is soaked with a liquid, compromised, torn, ripped, or otherwise damaged.

The cables 138, 144 are made of an electrically conductive material and may be permanently attached or removably attached to the electrically conductive surface 120. Attachment means 150 such as soldering with silver, or gold materials or the like may be used to destructively attach the cables 138, 144 to the electrically conductive surface 120. Patient health monitoring cables 138, 144 or lead wires, are well known in the healthcare industry, and may be used to nondestructively attach the cables 138, 144 to the electrically conductive surface 120 through electrodes 152.

Figure 10:
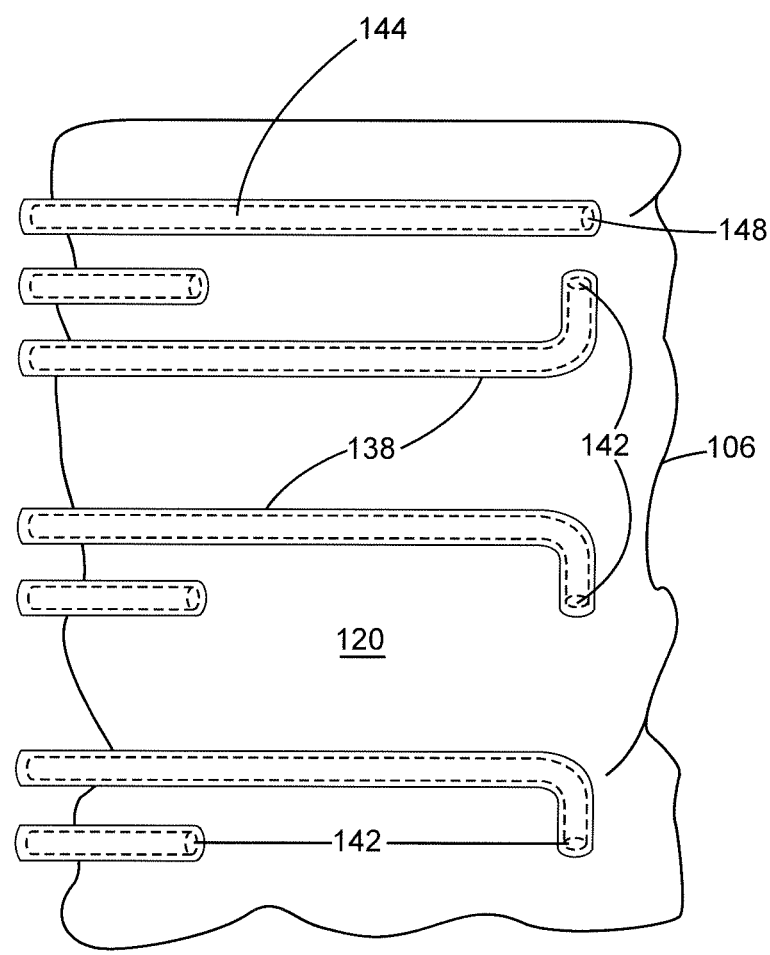
FIG. 10 is an illustration of a sensing device in accordance with another example of the present disclosure.

The cables 138, 144 may also be physically integrated with the covering 106 as illustrated in FIG. 10. In this example, the cables 138, 144 can be fabricated out of the same material as the covering as described above and may be sewn, adhered, stapled, or otherwise attached to the covering 106. A two layered structure is formed when the cables 138, 144 are integrated into the covering 106. This configuration is compact and requires fewer components to assemble in the field, thus improving manufacturing and installation efficiencies.

The electrodes 152 are also made of an electrically conductive material and may be destructively attached or nondestructively attached to the electrically conductive surface 120. Attachment means 150 such as soldering with silver, or gold materials or the like may be used to permanently attach the electrodes 152 to the electrically conductive surface 120. Adhesive backed electrodes 152 are typically used in the healthcare industry, and these may be used in this particular application as well.

Electrocardiography (ECG) electrodes 152 are relatively inexpensive and contain a protruding stud that cooperates with a complimentary socket in the cables 138, 144 to make an electrically conductive connection. This configuration forms an attachment and detachment mechanism, while ensuring that electrical conductivity exists between the components. An exemplary electrode 152 of this type is described in U.S. Patent Application Publication 2012/0196474, Ser. No. 13/443,096, and is included herein by reference.

Figure 11:
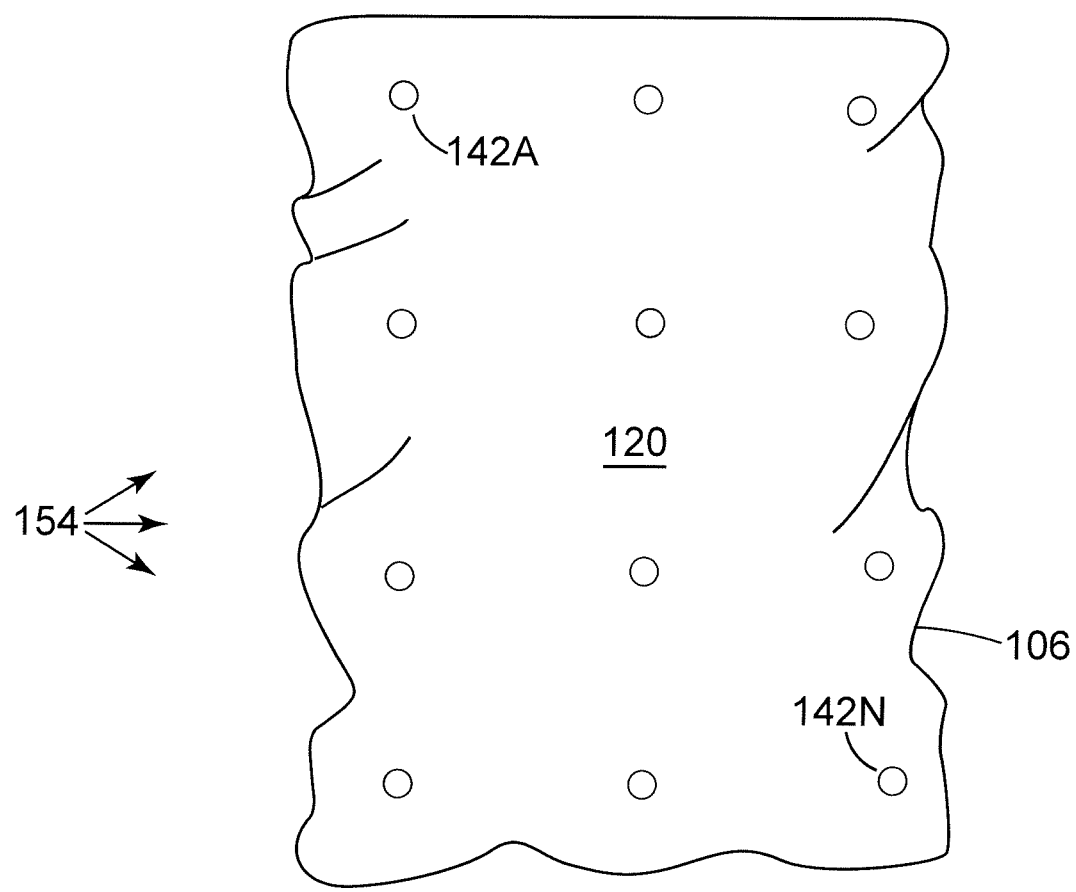
FIG. 11 is an illustration of an example of a covering having a rectangular pattern of measurement points.
Figure 12:
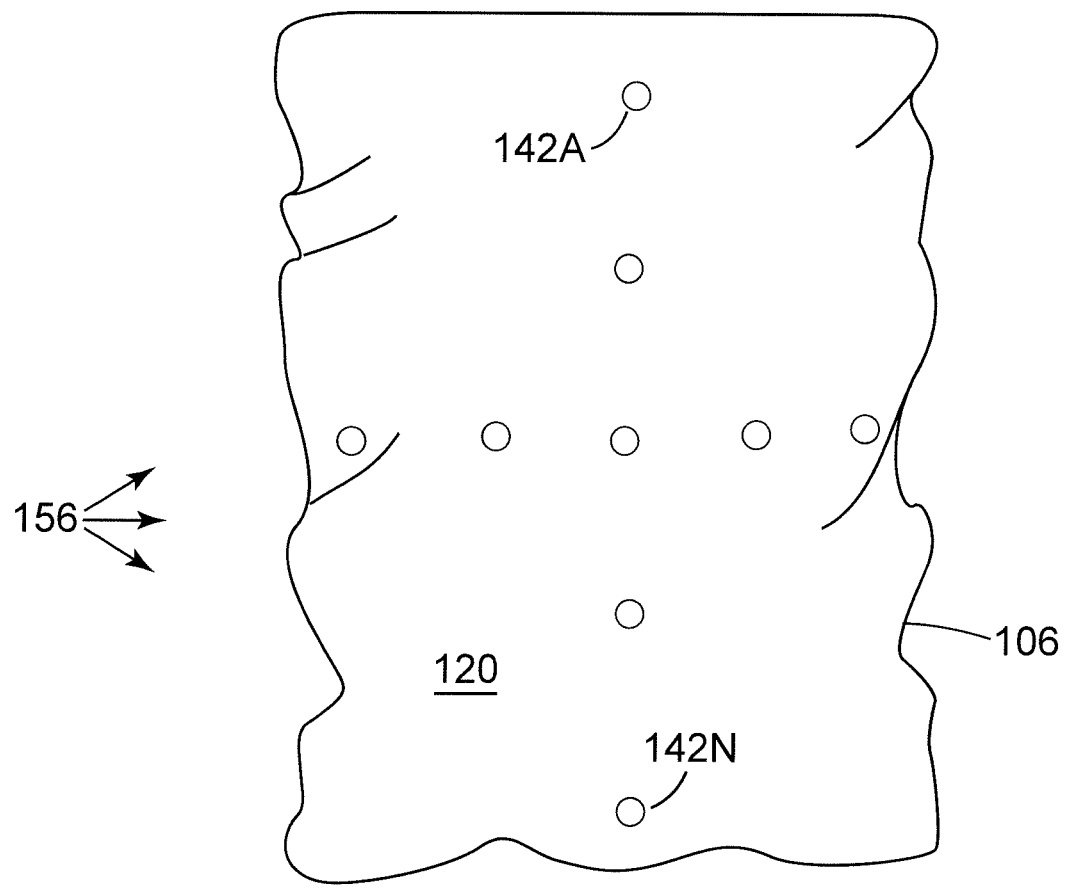
FIG. 12 is an illustration of an example of a covering having a cross pattern of measurement points.
Figure 13:
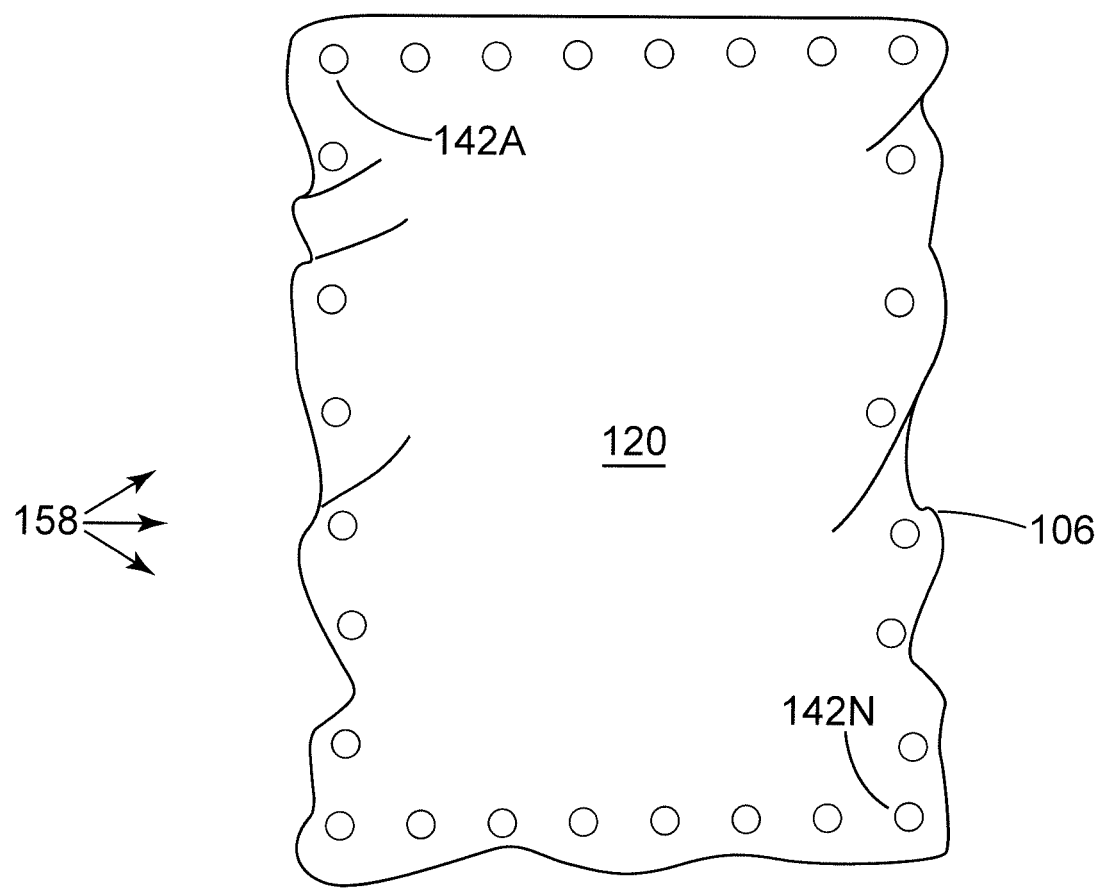
FIG. 13 is an illustration of an example of a covering having a peripheral pattern of measurement points.
Figure 14:
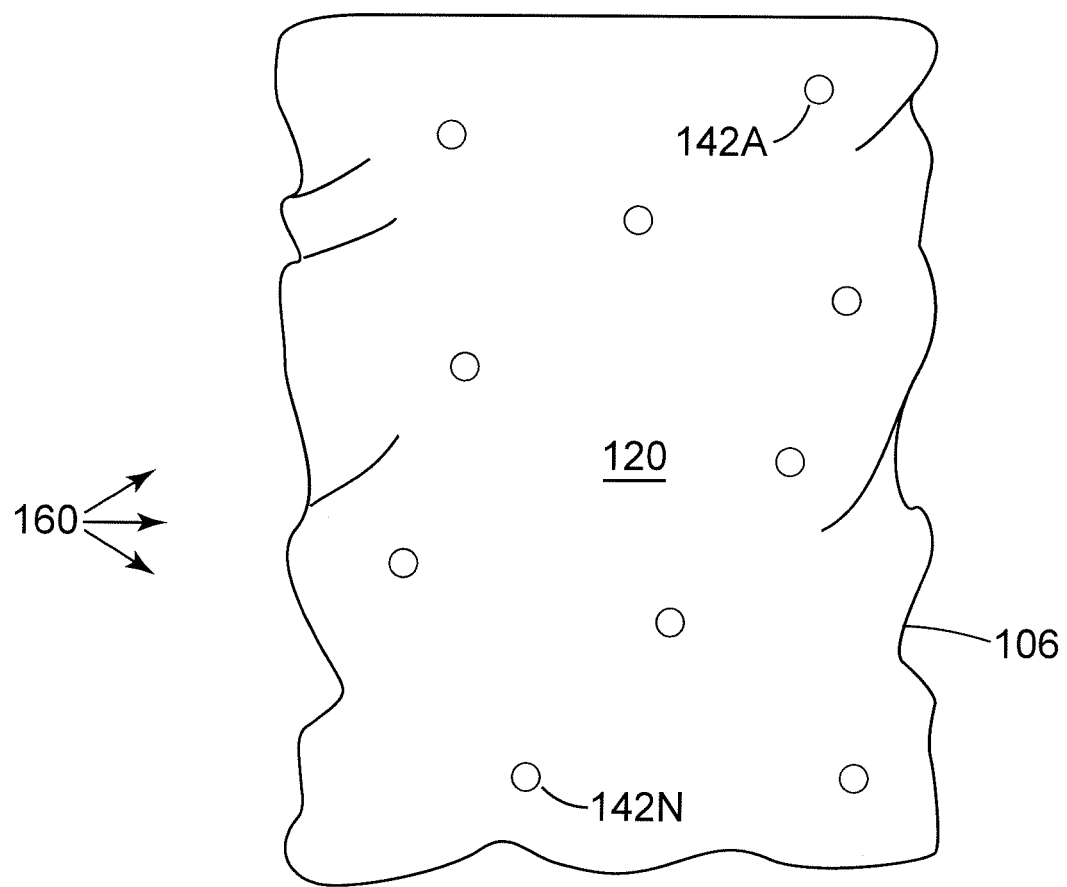
FIG. 14 is an illustration of an example of a covering having a random pattern of measurement points.

While a single measuring point 142 will detect tampering that occurs proximate to the area of the measuring point 142 and the common point 148, a plurality of measuring points 142A, 142B, . . . , 142N increases the area that can effectively be measured by the sensing device 108. For example, a rectangular pattern 154 of measuring points 142 may extend across the electrically conductive surface 120 as shown in FIG. 11, a cross pattern 156 of measuring points 142 may extend across the electrically conductive surface 120 as shown in FIG. 12. A peripheral pattern 158 of measuring points 142 may extend across the electrically conductive surface 120 as shown in FIG. 13. A random pattern 160 of measuring points 142 may extend across the electrically conductive surface 120 as shown in FIG. 14. The pattern examples illustrated are merely exemplary, not considered to be exhaustive, and other patterns and combinations of patterns are also contemplated. Covering 106 size, shape and monitoring accuracy will determine the pattern size and density.

Figure 15:
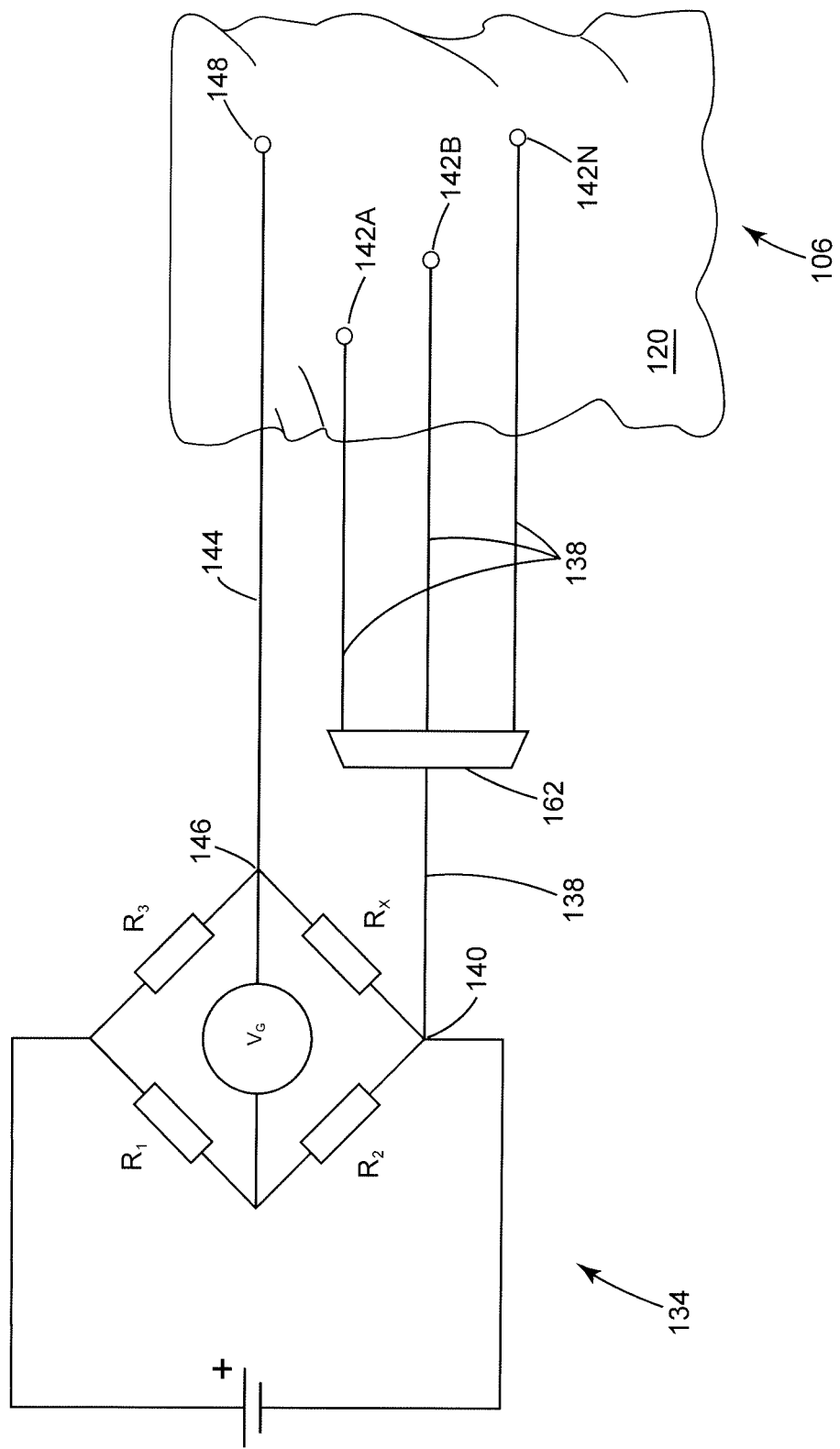
FIG. 15 is an illustration of an example of a sensing device with multiplexor circuitry.
Figure 16:
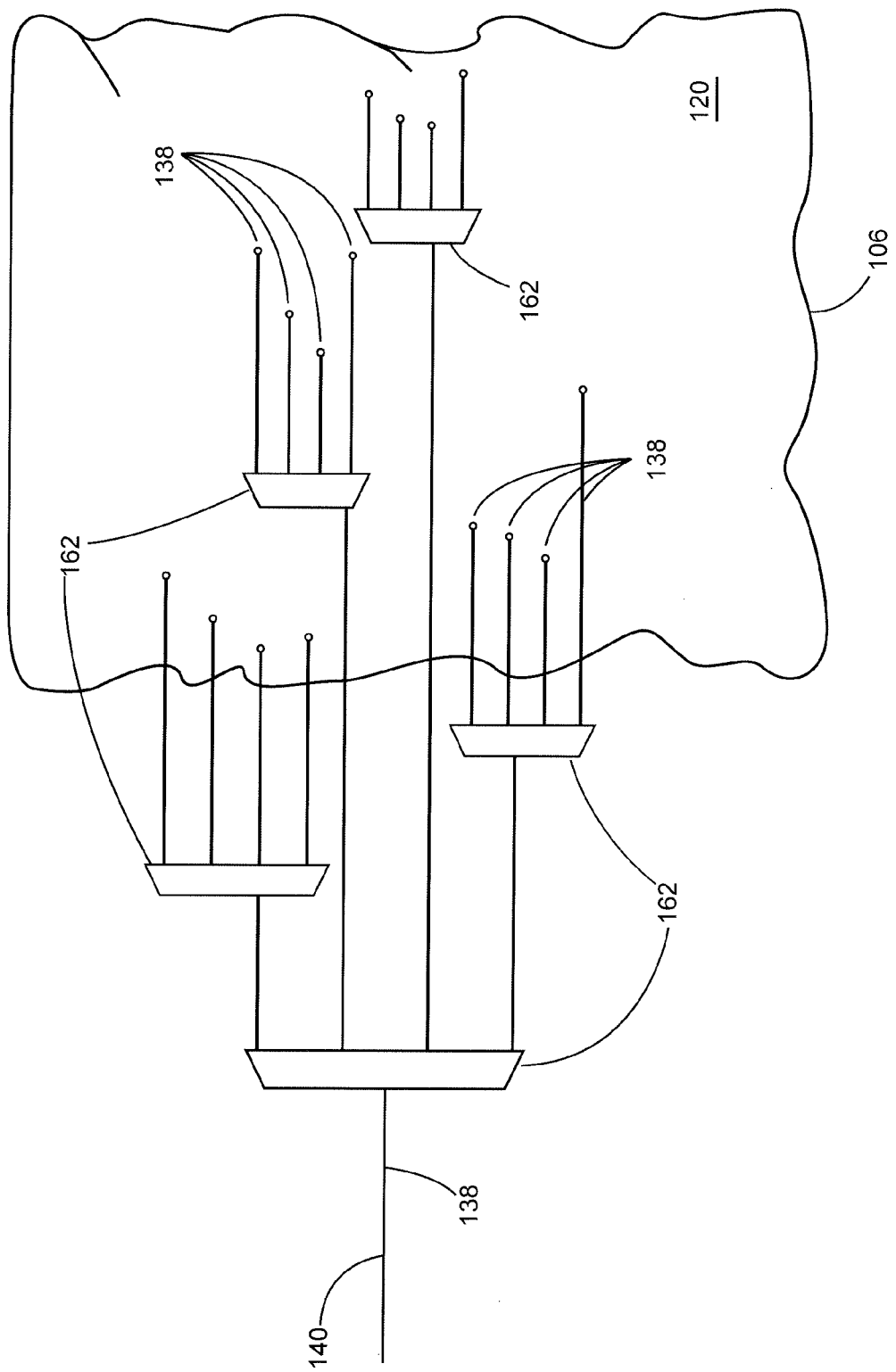
FIG. 16 is a schematic illustration of several multiplexers arranged in a parallel configuration.

In order to monitor a plurality of measuring points 142 with the single, Wheatstone bridge circuit 134, a multiplexer 162 is electrically coupled between a plurality of measuring points 142 (inputs) and the first end 140 (output) of the measured resistance leg $R_X$ of the Wheatstone bridge circuit 134. See FIG. 15 for a more detailed illustration of this particular configuration. The multiplexer 162 alternately selects a single measuring point 142 (input), from the plurality of measuring points 142A-142N (inputs), and connects that single point 142 to the first leg 140 of the measured resistance $R_X$. Several, individual multiplexers 162 may be connected together in parallel to increase the number of measuring points 142 (inputs) that may be monitored. See FIG. 16 for an example of a configuration having five multiplexers and sixteen monitoring points. Electrical connections between the plurality of measuring points 142A-142N and the multiplexers 162 are made with cables 138 and electrodes 152 as described above.

In operation, the multiplexer 162 electrically connects exactly one of the measuring points 142 to the first end 140 of the measured resistance leg $R_X$ of said Wheatstone bridge circuit 134 at a time. The multiplexer 162 can alternate the connection to each of the plurality of measuring points 142A-142N either sequentially, according to a pattern, or purely at random. Please note that there is still only one common point 148, which is directly connected to the second end 146 of the measured resistance leg $R_X$ of said Wheatstone bridge circuit 134.

Figure 17:
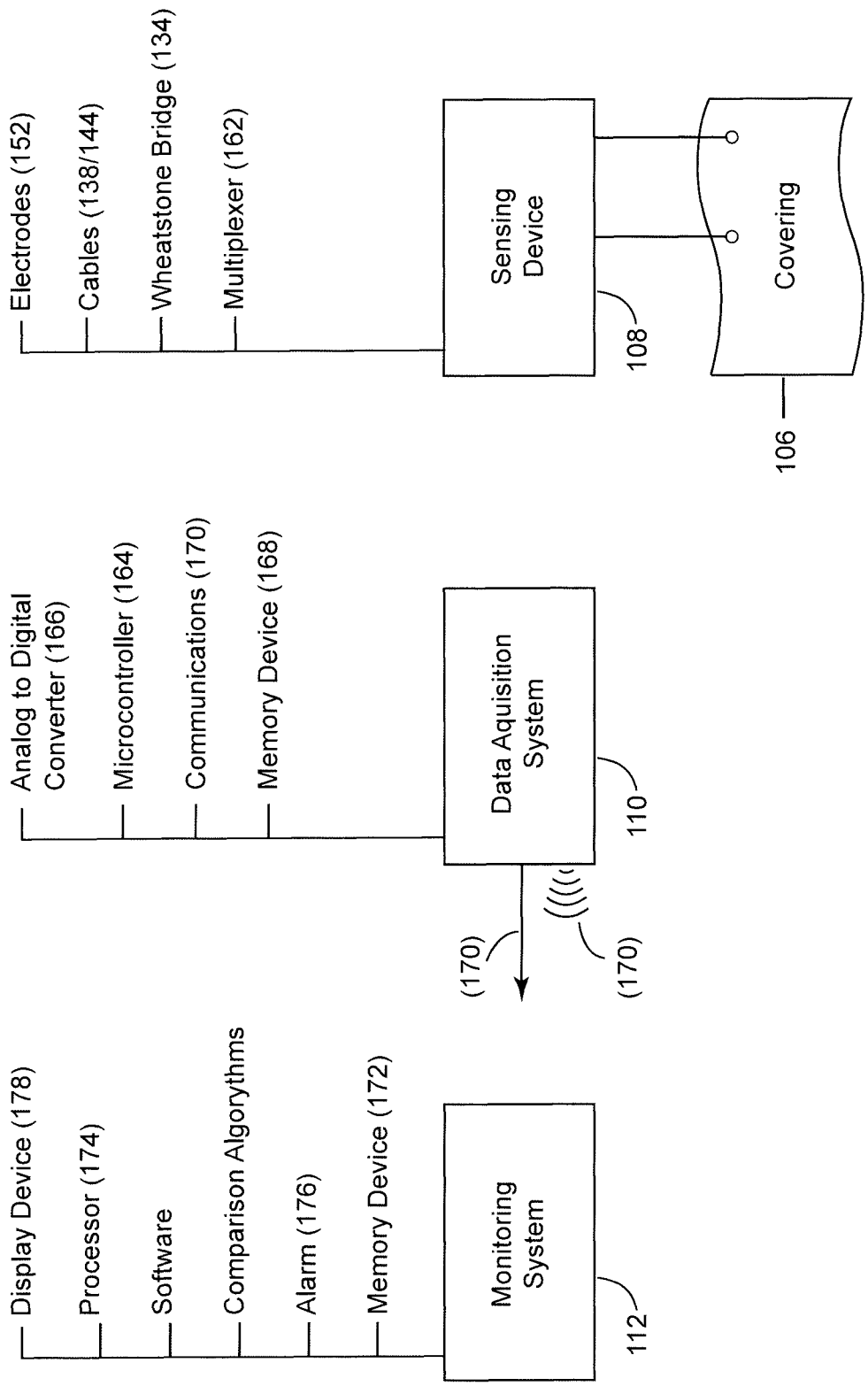
FIG. 17 is a highly schematic illustration of a conductive fabric seal device in accordance with an example of the present disclosure.

The analog voltage signals ($V_G$) are sent to a data acquisition system 110 for processing as schematically illustrated in FIG. 17. The data acquisition system 110 includes a microcontroller 164, which operates the sensing device 108. Also included is an analog to digital converter (ADC) 166, which converts the analog voltage ($V_G$) to a digital value that is indicative of the voltage ($V_G$) for a particular measuring point 142 at a specific time. The digital voltage value ($V_G$) is then stored in a memory device 168. The memory device 168 may include nonvolatile memory (e.g., memory cards, flash drives, solid-state devices, ROM/PROM/EPROM/EEPROM, etc.), or volatile memory (e.g., RAM/DRAM, etc.) for example.

Once the digital voltage value ($V_G$) is stored, the value is sent to a monitoring system 112 for processing. Individual voltage values ($V_G$), or multiple voltage values ($V_G$) may be sent to the monitoring system 112 in real time or according to a schedule. For example, stored values may be sent at intervals such as once a second, once a minute, once an hour, or once a day. Other intervals are also contemplated.

The digital voltage values ($V_G$) are sent to the monitoring system 112 via a communication means 170. The communication means 170 include either wired or wireless devices and methods. Wireless communication means 170 such as radio, microwave, visible light, sonic or electromagnetic induction and the like may be used. Wired communication means such as telephone networks, cable networks, internet networks and the like may also be used. The digital voltage values ($V_G$) are sent via the communication means 170 in either unencrypted format or encrypted format for improved security.

Once a digital voltage value ($V_G$) arrives at the monitoring system 112, the value is used to calculate the measured resistance ($R_X$), between the measuring point 142 and the common point 148, according to the following equation.

$$R_X=(R_2*R_3+R_3*(R_1+R_2)V_G/V_{in})/(R_1-(R_1+R_2)*V_G/V_{in})$$

The calculated resistance ($R_X$) for a specific measuring point 142 is then compared to the known, nominal, resistance ($R_{nominal}$) for that same measuring point 142. If the measured and nominal resistance values are equal to one another, or within an appropriate tolerance, this is indicative of the covering 106 having a condition that is normal and not tampered with. In this particular example, no alert is generated. If, however, the measured and nominal resistance values are not equal to one another, or within a certain tolerance (e.g. +/−0.5%, +/−1.0%, +/−>1%), this is indicative of the covering 106 having a condition that is tampered with and not normal. In this particular example, an alert is generated. Note that the calculated resistance will change if the covering 106 is subjected to ripping, tearing, etc. . . . , as discussed earlier, as well as during leakage of the article itself (liquid, gas or solid).

The monitoring system 112 includes a readable medium 172 that has stored on it a series of preprogrammed instructions that, when executed, cause a processor 174 to make the ($R_X$) calculations and comparisons described immediately above. The readable medium 172 also stores the ($R_X$) values for future review and analysis.

A "computer-readable medium," "machine-readable medium," "propagated-signal" medium, and/or "signal-bearing medium" may comprise a non-transitory readable medium 172 that contains or stores software for use by or in connection with an instruction executable system, apparatus, device, or processor 174. The readable medium 172 may selectively be, but not limited to, an electronic, magnetic, optical, electromagnetic, infrared, or semiconductor system, apparatus, device, or propagation medium. A non-exhaustive list of examples of a readable medium 172 would include: an electrical connection having one or more wires, a portable magnetic or optical disk, a volatile memory such as a Random Access Memory (RAM), a Read-Only Memory (ROM), an Erasable Programmable Read-Only Memory (EPROM or Flash memory), or an optical fiber. A readable medium 172 may also include a tangible medium upon which software is printed, as the software may be electronically stored as an image or in another format (e.g., through an optical scan), then compiled, and/or interpreted or otherwise processed. The processed medium may then be stored in a computer and/or machine memory.

As illustrated in FIG. 17, the monitoring system 112 may be sited locally or remotely from the asset or article 100. The monitoring system 112 may monitor a single or a plurality of articles 100. The monitoring system may include a signaling means 176 to alert an observer if the ($R_X$) value is indicative of the covering 106 having a condition that is tampered with and not normal. Signaling means 176 such as one or more of a wired or wireless electronic alert (e.g., email, fax, page, text message, etc. . . . ), an audible alert, or a visible alert may be used to signal an observer.

The monitoring system 112 may be physically located in mobile cell phones, wireless phones, personal digital assistants, two-way pagers, smartphones, portable computers, tablets, personal computers, a laptop computer, and other devices, for example.

Figure 18:
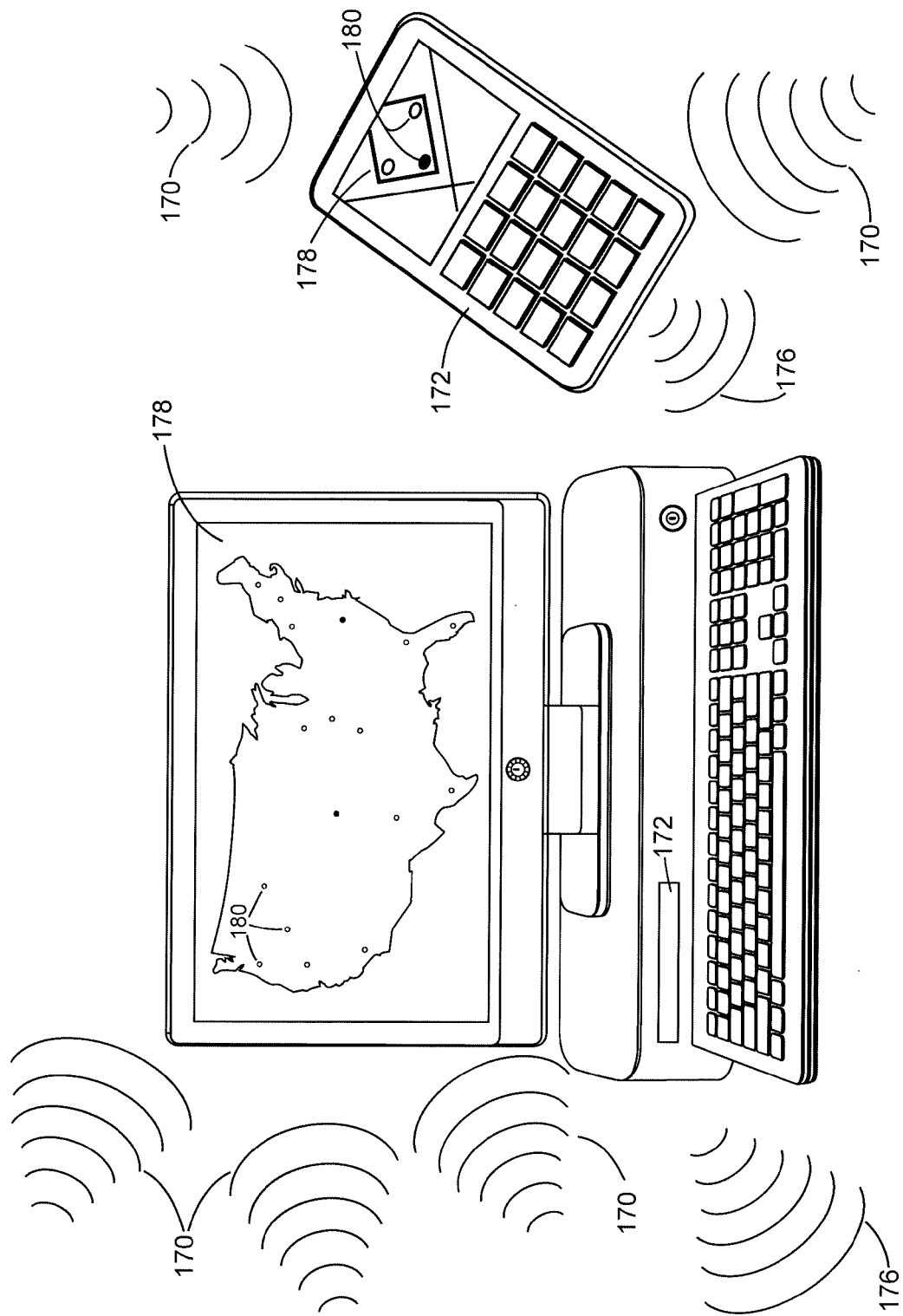
FIG. 18 is an illustration of a monitoring device in accordance with an example of the present disclosure.

The monitoring system 112 may also exhibit on a display device 178 an article's 100 location on a map, as determined from a Global Positioning Satellite, with a status indicator 180 of its current condition. For example, the status indicator 180 may be displayed as a green colored icon if the article 100 is in a normal and not tampered with condition, and the status indicator 180 may change to a red colored icon if the article has a condition that is tampered with and not normal. See FIG. 18 for examples of such displays 178.

Figure 19:
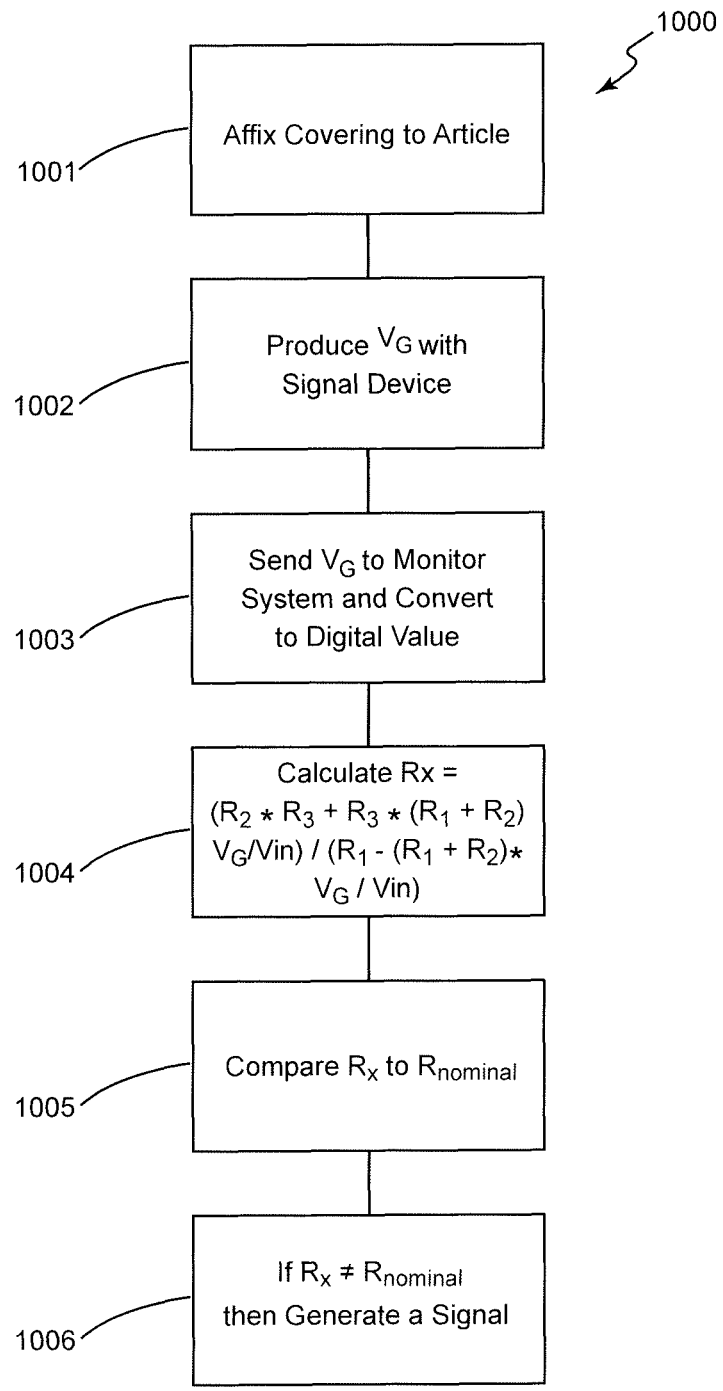
FIG. 19 is a schematic illustration of a method for monitoring the condition of an article in accordance with an example of the present disclosure.

A schematic representation of a method 1000 for monitoring the condition of an article is schematically illustrated in FIG. 19. In this method, conditions such as breakage, tampering, leakage of material, etc. . . . may be monitored. In a first step, represented by 1001, a covering 106 is affixed around an article 100 to be monitored with fastening means 126. In the next step, represented by 1002, a sensing device 108, which is affixed to the covering 106 produces an analog voltage value ($V_G$). In the next step, represented by 1003, the analog voltage value ($V_G$) is sent to a data acquisition system 110, where it is converted into a digital voltage value ($V_G$). Once converted to a digital value, the voltage ($V_G$) is sent to a monitoring system 112, which calculates a measured resistance $R_X$ according to the equation $R_X=(R_2*R_3+R_3*(R_1+R_2)V_G/V_{in})/(R_1-(R_1+R_2)*V_G/V_{in})$ as represented by step 1004. Once the measured resistance ($R_X$) is calculated, it is compared to a known, nominal resistance ($R_{nominal}$) as represented by step 1005. If the measured resistance ($R_X$) is not equal to the known, nominal resistance ($R_{nominal}$), within a certain tolerance (e.g. +/−0.5%, +/−1.0%, +/−>1%), then signaling means generates an alert as represented in final step 1006. Note that this method is repeated for each of the one or more measuring points 142 and according to a schedule (e.g., continuous, hourly, daily, etc. . . . ).

While this disclosure describes and enables several examples of systems and methods for detecting if an article is being tampered with, other examples and applications are contemplated. Accordingly, the invention is intended to embrace those alternatives, modifications, equivalents, and variations as fall within the broad scope of the appended claims. The technology disclosed and claimed herein may be available for licensing in specific fields of use by the assignee of record.

What is claimed is:

1. A method for monitoring the condition of an article comprising the steps of:
  a. affixing a covering made of a substrate that is coated with a layer of an electrically conductive material and forming a single electrically conductive surface that extends over the entire covering and has an electrical resistance, said covering being configured to at least partially encapsulate the article such that the article cannot be tampered with, without modifying the electrical resistance of said covering;
  b. producing an analog voltage value ($V_G$) with a sensing device that is affixed to the electrically conductive surface of said covering;
  c. converting the analog voltage value ($V_G$) into a digital voltage value ($V_G$) with a data acquisition system;
  d. calculating a measured resistance $R_X$ from the digital voltage value ($V_G$), the power supply ($V_{in}$) and known resistances ($R_1$), ($R_2$) and ($R_3$) according to the equation $R_X=(R_2*R_3+R_3*(R_1+R_2)V_G/V_{in})/(R_1-(R_1+R_2)*V_G/V_{in})$ with a monitoring system;
  e. comparing the measured resistance ($R_X$) to a known, nominal resistance ($R_{nominal}$) with the monitoring system; and
  f. generating an alert with a signaling means if the measured resistance ($R_X$) is greater than the known, nominal resistance ($R_{nominal}$).

2. The method of claim 1 wherein the sensing device of step b) includes a Wheatstone bridge circuit and at least one multiplexer.

3. The method of claim 1 wherein the alert generated in step f) includes a color coded icon that is exhibited on a display device and represents the current condition of the article.

4. The method of claim 1 wherein the monitored condition is a leakage of a liquid, a gas, or a solid from the article.

5. The method of claim 2 wherein one of the at least one multiplexer is electrically connected to a first end of a resistance leg of said Wheatstone bridge circuit, the multiplexer also being electrically connected to one or more measuring points on the electrically conductive surface by a measuring cable attached to each measuring point; and wherein the multiplexer is configured to electrically connect exactly one of the measuring cables to the first end of the resistance leg of said Wheatstone bridge circuit at a time and is able to alternate connections to each of the measuring cables.

6. The method of claim 1 wherein said covering substrate of step a) comprises a fabric that is made from a material that is electrically insulative.

7. The method of claim 6 wherein said covering substrate is coated with an electrically conductive metallic material on one side of the substrate such that said covering is metallized.

8. The method of claim 6 wherein said covering substrate is coated with an electrically conductive metallic material on both sides of the substrate such that said covering is metallized.

9. The method of claim 5 wherein said cables are each connected to the electrically conductive surface through an electrode.

10. The method of claim 5 wherein said cables are each integrated with said covering.

11. The method of claim 1 wherein the affixing step a) includes a fastening means to secure said covering to the article.

12. The method of claim 1 wherein the monitoring system of calculating step d) includes a non-transitory readable medium, a processor, and a display device.

13. The method of claim 1 wherein the covering of affixing step a) protects the article from electromagnetic interference.

14. The method of claim 2 wherein the measuring points are disposed in a rectangular pattern on the electrically conductive surface.

15. The method of claim 2 wherein the measuring points are disposed in a cross pattern on the electrically conductive surface.

16. The method of claim 2 wherein the measuring points are disposed in a peripheral pattern on the electrically conductive surface.

17. The method of claim 2 wherein the measuring points are disposed in a random pattern on the electrically conductive surface.

* * * * *